(12) United States Patent
Cho et al.

(10) Patent No.: US 8,137,939 B2
(45) Date of Patent: Mar. 20, 2012

(54) METHOD OF RECOVERING L-THREONINE FROM L-THREONINE FERMENTATION BROTH USING NONSOLVENT

(75) Inventors: Gyu-Nam Cho, Incheon (KR);
Won-Seop Choi, Seoul (KR);
Yong-Bum Seo, Seoul (KR);
Seung-Woo Han, Seoul (KR); Yoo-Shin Kim, Seoul (KR); Moung-Ki Shin, Seoul (KR); Hee-Sung Park, Gwangmyeong (KR); Soon-Won Hong, Seoul (KR)

(73) Assignee: CJ Cheiljedang Corp. (KR)

( * ) Notice: Subject to any disclaimer, the term of this patent is extended or adjusted under 35 U.S.C. 154(b) by 351 days.

(21) Appl. No.: 12/516,278

(22) PCT Filed: Nov. 27, 2007

(86) PCT No.: PCT/KR2007/006024
§ 371 (c)(1),
(2), (4) Date: May 26, 2009

(87) PCT Pub. No.: WO2008/066307
PCT Pub. Date: Jun. 5, 2008

(65) Prior Publication Data
US 2010/0047882 A1  Feb. 25, 2010

(30) Foreign Application Priority Data

Nov. 27, 2006  (KR) .................. 10-2006-0117947

(51) Int. Cl.
*C12P 13/08*  (2006.01)

(52) U.S. Cl. ........................................ 435/115
(58) Field of Classification Search ............ 435/115
See application file for complete search history.

(56) References Cited

U.S. PATENT DOCUMENTS

| 5,087,566 | A | 2/1992 | Takano et al. |
| 5,264,353 | A | 11/1993 | Yamada et al. |
| 2005/0054076 | A1 | 3/2005 | Cho et al. |
| 2005/0124048 | A1 | 6/2005 | Akhverdian et al. |
| 2005/0164357 | A1 | 7/2005 | Rieping |

FOREIGN PATENT DOCUMENTS

| KR | 10-2000-013854 | 3/2000 |
| KR | 10-2000-013855 | 3/2000 |

OTHER PUBLICATIONS

Zhang, Jinlong "Study on Crystallization Process of L-Threonine" ABS The Second International Workshop on Industrial Crystallization of China (2004) webmaster@crcce.com.*
International Search Report—PCT/KR2007/006024 dated Feb. 26, 2008.
Written Opinion—PCT/KR2007/006024 dated Feb. 26, 2008.

* cited by examiner

*Primary Examiner* — Herbert J Lilling
(74) *Attorney, Agent, or Firm* — Cantor Colburn LLP

(57) ABSTRACT

Provided are a method of recovering L-threonine from the fermentation broth of an L-threonine producing microorganism, comprising: separating microbial bodies from the L-threonine containing fermentation broth obtained by culturing an L-threonine producing microorganism and filtering the separated fermentation broth to obtain a filtrate; concentrating the filtrate; and reacting the concentrated filtrate with a nonsolvent to obtain crystalline L-threonine, crystalline L-threonine recovered by the method, and a feed additive containing the crystalline L-threonine recovered by the method.

6 Claims, 3 Drawing Sheets

METHOD OF RECOVERING L-THREONINE FROM L-THREONINE FERMENTATION BROTH USING NONSOLVENT

CROSS-REFERENCE TO RELATED PATENT APPLICATION

This application claims the benefit of Korean Patent Application No. 10-2006-0117947, filed on Nov. 27, 2006, in the Korean Intellectual Property Office, the disclosure of which is incorporated herein in its entirety by reference.

BACKGROUND OF THE INVENTION

1. Field of the Invention

The present invention relates to a method of recovering L-threonine from the fermentation broth of an L-threonine producing microorganism by using a nonsolvent, and more particularly, to a method of recovering crystalline L-threonine by using a drowning-out process in which the fermentation broth of an L-threonine producing microorganism is filtered and the filtrate is concentrated and reacted with a nonsolvent to crystallize L-threonine, crystalline L-threonine recovered using the method, and a feed additive containing the crystalline L-threonine.

2. Description of the Related Art

L-threonine, which is an essential amino acid, is mainly used in complete amino acid formulations, nutritional supplements, and the like. Recently, L-threonine has been used as an additive to animal feed together with L-lysine, and thus the demand for L-threonine has increased.

L-threonine is mainly produced by fermentation and concentration-crystallization. That is, microbial bodies are removed from the fermentation broth of L-threonine producing microorganisms by filtration or centrifugal separation, the pH of the obtained filtrate is adjusted, and then the pH-adjusted filtrate is concentrated with solvent being removed to recover crystalline L-threonine in the form of a needle.

However, when the concentration-crystallization method is used, the recovery yield of crystalline L-threonine is low. In the concentration-crystallization method, to maintain separation efficiency of concentrated crystalline slurry and product quality, an L-threonine containing solution or broth is concentrated to the range of 50 to 70% of L-threonine. Since crystallization is performed by heating the filtrate of an L-threonine containing fermentation broth to evaporate a solvent, crystallization proceeds at a high temperature, and a large amount of L-threonine is dissolved in the filtrate, i.e, the mother solution accordingly. Thus, when the crystalline slurry is separated using a separator, a relatively large amount of L-threonine remains in the mother solution, and thus its recovery is impossible.

In addition, the needle-form of the crystalline L-threonine, generated in the concentration-crystallization method, creates a big disadvantage. In the absence of additives or nonsolvents, the crystalline form of L-threonine is thin, long, and needle shaped. Therefore, the crystalline L-threonine formed in the concentration-crystallization method is in the form of thin needle with a length of about 50 to 250 μm. Agglomeration in the crystalline slurry occurs between the L-threonine crystals in the form of a needle, and thereby the viscosity of the crystalline slurry is increased, resulting in a reduction in separation efficiency when the crystals are separated. If the separation efficiency is decreased, L-threonine productivity is decreased and impurities remain in L-threonine products, and thus the product quality is degraded. The L-threonine crystals in the form of a needle also reduce the flowability of the product, and thus this causes a lot of inconveniences when consumers use the product. Generally, consumers use L-threonine as an additive to animal feed. L-threonine is added to animal feed using a manual or automatic system. Here, a reduction in the flowability of L-threonine causes problems in use of such a manual or automatic animal feed mixing system, and this often leads to claims of consumers. In addition, the strong tendency of the L-threonine crystals in the form of a needle to agglomerate leads to lumping and caking during long-term storage and transportation. Due to the agglomeration, consumers may sometimes have to process the agglomerated L-threonine products to obtain L-threonine before using them. In an era of global competition, any claims from consumers and consequent harm to product reputation may constitute as serious problems as weaken the foundation of business. Thus, the low flowability of the L-threonine crystals in the form of a pillar can serve as a serious disadvantage.

Korean Patent Publication No. 2000-0013855 discloses a method of purifying L-threonine from an L-threonine fermentation broth by recrystallization. However, this method is performed in four steps so that the process is excessively complicated with a lot of equipment required. In addition, an ion exchange resin tower is used in order to recover the loss of a mother solution, and thus a large amount of acid, base and water is used. In addition, in all steps of crystallization, a concentration-crystallization process is used to form the L-threonine crystals in the form of a needle, resulting in low flowability of L-threonine products.

Korean Patent Publication No. 2000-0013854 discloses a method of purifying L-threonine using electrodialysis. This method may reduce an amount of acid, base and water used compared to a conventional ion exchange resin method. However, since an L-threonine solution passing through an electrodialyzer is concentrated under reduced pressure to produce an L-threonine product in the form of a needle, the flowability of the product is low. In addition, compared to the case of directly concentrating a filtrate of a microbial fermentation broth, it takes over 6 hours to pass through the electrodialyzer. Thus, the productivity of the L-threonine product is low.

Therefore, there is still a need to develop an improved method of recovering L-threonine, which can solve the inconveniences of consumers that are caused by the low recovery yield of L-threonine from fermentation broth, and the low flowability of the L-threonine product as a result of the L-threonine crystal shapes.

SUMMARY OF THE INVENTION

The present invention provides a method of recovering crystalline L-threonine from the fermentation broth of an L-threonine producing microorganism by drowning-out crystallization.

The present invention also provides a crystalline L-threonine recovered by drowning-out crystallization using a nonsolvent.

The present invention also provides feed additives containing the crystalline L-threonine recovered by drowning-out crystallization using a nonsolvent.

According to an aspect of the present invention, there is provided a method of recovering L-threonine from a fermentation broth of an L-threonine producing microorganism, the method comprising: separating microbial bodies from the L-threonine containing fermentation broth that is obtained by culturing an L-threonine producing microorganism and filtering the broth to obtain a filtrate; concentrating the filtrate; and reacting the concentrated filtrate with a nonsolvent to obtain L-threonine crystals.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
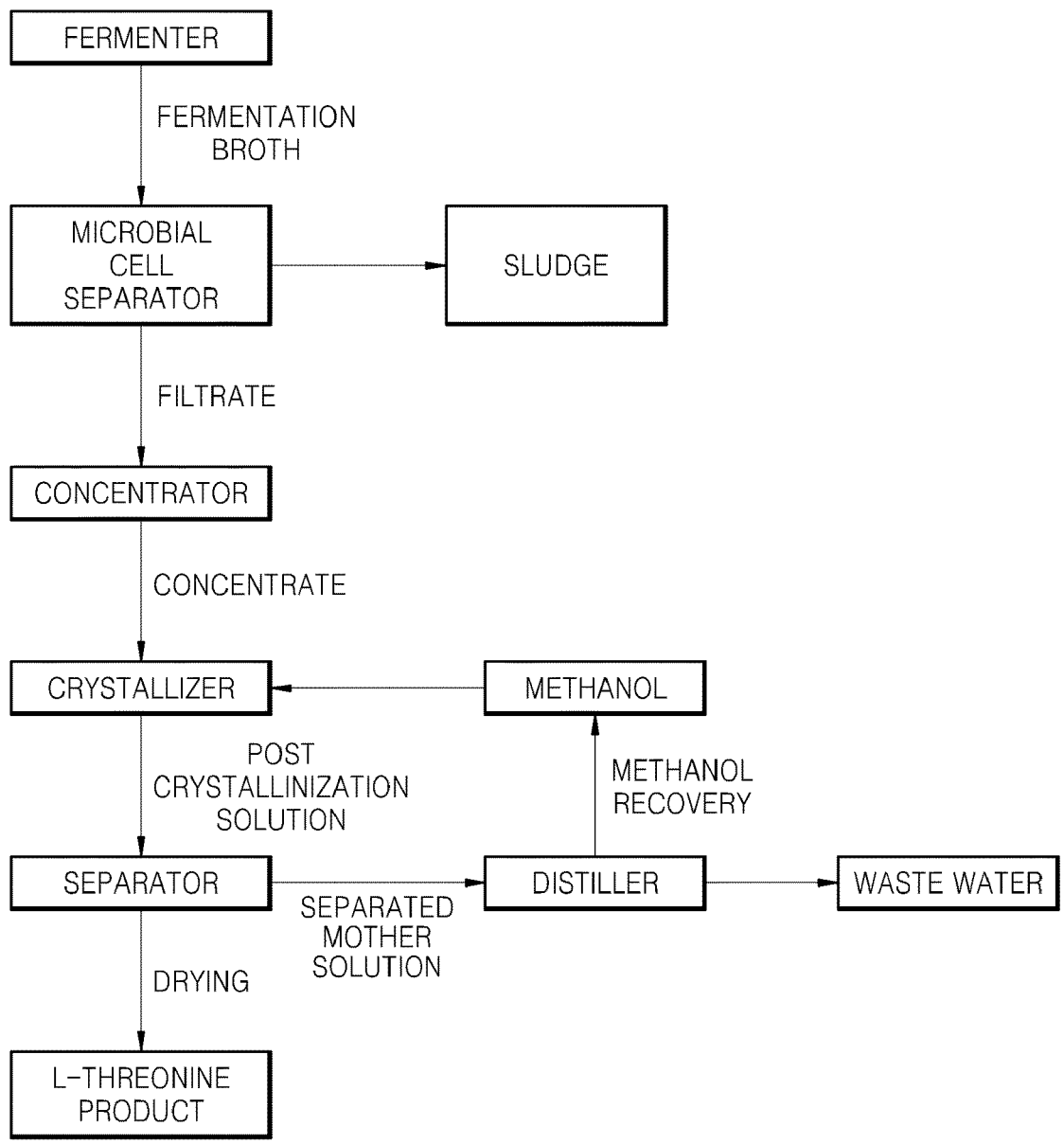
FIG. 1 is a schematic flowchart showing a method of recovering L-threonine, according to an embodiment of the present invention.

The method of recovering L-threonine from a fermentation broth of a microorganism comprises: separating microbial bodies from the L-threonine containing fermentation broth that is obtained by culturing an L-threonine producing microorganism and filtering the broth to obtain a filtrate; concentrating the filtrate; and reacting the concentrated filtrate with a nonsolvent to obtain L-threonine crystals.

The microbial bodies used in fermentation in order to prepare the L-threonine containing fermentation broth may be any microbial bodies which can produce L-threonine.

According to an embodiment of the present invention, the microbial bodies used in producing L-threonine may be a transformed strain of *Escherichia coli*. The transformed strain is cultured in a slant medium to obtain a seed culture, and then using the seed culture, preculture and main culture are performed to finally produce the fermentation broth containing L-threonine. The produced fermentation broth may contain 5 to 15 wt % of L-threonine.

According to an embodiment of the present invention, the separating of the microbial bodies from the fermentation broth of a microorganism may be performed by a method selected from the group consisting of filtration, centrifugal separation, and heat treatment.

According to an embodiment of the present invention, the fermentation broth is filtered by membrane filtration, and thus is separated into a filtrate and sludge containing the microorganisms. The membrane filtration is conducted to remove the microbial bodies in the fermentation broth. In the membrane filtration, the microbial bodies that can not pass through pores of the membrane and extra impurities are removed from the fermentation broth and only a solution that can pass through the pores of the membrane is obtained as the filtrate. Herein, the residue that can not pass through the pores of the membrane, and thus is not obtained as the filtrate, is referred to as sludge, and the sludge can be discarded in a process of purifying L-threonine.

A membrane filter used in the membrane filtration may be any filter which can separate the microbial bodies from the fermentation broth. The operation conditions of the membrane filter can easily be set by those of ordinary skill in the art in order to separate the microbial bodies from the fermentation broth. For example, the fermentation broth may be heated to about 60° C. in advance under a trans membrane pressure (TMP) of 1.2 to 1.5. The TMP refers to a value representing the intensity of pressure which is applied in a horizontal direction against a solution flowing in a vertical direction, and denotes pressure given to the membrane filter by the solution in the membrane filter. The size of the pores of the membrane filter used can easily be selected by those of ordinary skill in the art.

According to an embodiment of the present invention, a gel layer may be formed in about 1 hour after the membrane filtration begins. The gel layer formation is to maintain the permeate flux of the filtrate at a certain level for a long period of time by forming a thin layer of the microbial bodies on a surface of the filtration membrane. If a gel layer is not formed, the permeate flux of the filtrate rapidly decreases, and thus the filtrate can not be appropriately obtained and the membrane filter must be washed more frequently. After the formation of the gel layer is completed, the filtrate is obtained through the membrane filter.

The filtrate obtained through the membrane filtration is concentrated. The concentration process is to reduce the burden on subsequent processes by decreasing the amount of the filtrate, and the concentration process is also to facilitate the crystalline formation by increasing the concentration of L-threonine in the filtrate.

The method of recovering L-threonine from the fermentation broth of microorganisms according to the present invention includes concentrating the filtrate obtained by separating the L-threonine producing microbial bodies from the fermentation broth.

The process of concentrating the filtrate obtained after the microbial bodies are separated may be performed by concentration under reduced pressure. Preferably, the concentration under reduced pressure may be performed in a concentrator at a temperature of 65 to 75° C. under a vacuum pressure of 680 to 700 mmHg. The conditions of the concentration under reduced pressure may be adjusted depending on concentration progress or in order to adjust the progress speed.

According to an embodiment of the present invention, the amount of total solids in the filtrate may be adjusted to the range of 20 to 30 wt % by concentration.

According to an embodiment of the present invention, the amount of L-threonine in the concentrated filtrate may be in the range of 5 to 25 wt %. Preferably, the amount of L-threonine in the concentrated filtrate may be in the range of 10 to 15 wt %.

The method of recovering L-threonine from the fermentation broth of a microorganism according to the present invention includes reacting the concentrated filtrate with a nonsolvent to obtain L-threonine crystals.

The L-threonine crystals can be obtained from the L-threonine containing concentrated filtrate by drowning-out crystallization using nonsolvent. In the drowning-out crystallization, the solubility of a target material dissolved in a solution is rapidly reduced using nonsolvent, and thus high supersaturation is easily induced at room temperature, resulting in recovery of the crystals of target material with a high yield. The term "nonsolvent" used herein refers to a solvent in which the target material is not soluble to a detectable level.

In an embodiment of the present invention, the nonsolvent may be at least one solvent selected from the group consisting of methanol, ethanol, propanol, isopropanol, and mixtures thereof. Preferably, the nonsolvent used in the present invention may be methanol.

Figure 2:
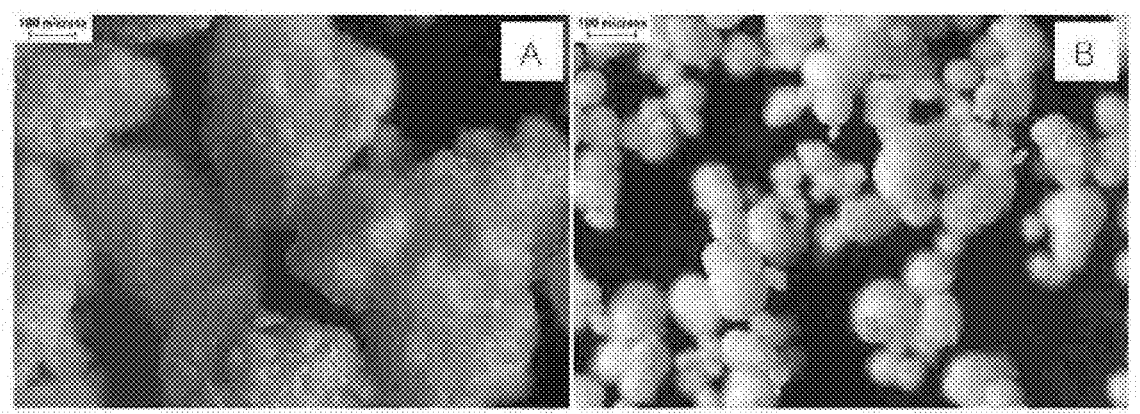
FIG. 2A is an microscopic image of a drowned-out resultant obtained by injecting methanol as a nonsolvent into a concentrated filtrate.
FIG. 2B is a microscopic image of a drowned out resultant obtained by injecting a concentrated filtrate into methanol as a nonsolvent.

The supersaturation of the target crystals in the drowning-out crystallization may be formed by two methods. One is to add a solution containing a target material (for example, filtered and concentrated fermentation broth containing L-threonine) to the nonsolvent (for example, methanol). The other is to add the nonsolvent to the solution containing the target material. That is, when the nonsolvent is put in a crystallizer, the L-threonine concentrate, to be later added to the nonsolvent in the crystallizer, is put in a raw material storage tank, on the other hand, when the L-threonine concentrate is put in the crystallizer, methanol, to be later added to the L-threonine concentrate in the crystallizer, is put in the raw material storage tank. FIGS. 2A and 2B are microscopic images showing crystalline shapes depending on the method of forming a supersaturated state in drowning-out crystallization according to an embodiment of the present invention. FIG. 2A is an microscopic image of a drowned-out resultant obtained by injecting methanol as a nonsolvent into a concentrated filtrate, and FIG. 2B is a microscopic image of a drowned out resultant obtained by injecting a concentrated filtrate into methanol as a nonsolvent. As illustrated in FIGS. 2A and 2B, when the L-threonine concentrate put in the raw material storage tank is added to methanol put in the crystallizer at a constant flow rate, which is the procedure used to produce the resultant shown in FIG. 2B, harder and more spherical L-threonine crystals can be obtained.

According to an embodiment of the present invention, the reacting of the concentrated filtrate with the nonsolvent may be performed by adding the concentrated filtrate to the nonsolvent in the crystallizer.

According to an embodiment of the present invention, the reacting of the concentrated filtrate with the nonsolvent may be performed by adding the nonsolvent to the concentrated filtrate in the crystallizer.

According to an embodiment of the present invention, the concentrated filtrate or the nonsolvent may be added to the crystallizer at a flow rate of 1.0 to 5.0 g/min, and preferably 1.0 to 3.0 g/min. When the flow rate is higher than 3.0 g/min, the intensity of crystals gets weak, while when the flow rate is lower than 1.0 g/min, fine crystals are formed. Thus, the flow rate may preferably be maintained at 1.0 to 3.0 g/min.

Figure 3:
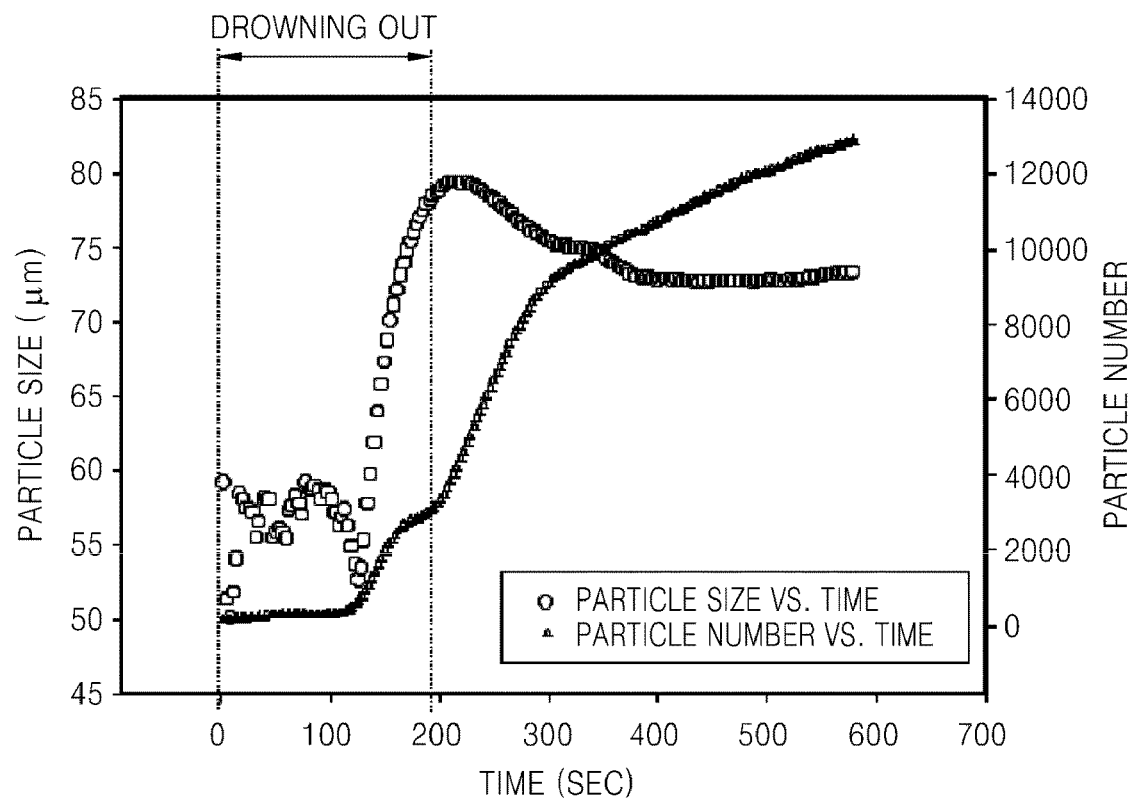
FIG. 3 is a graph showing how crystalline nucleation proceeds with time in drowning-out crystallization, which was observed using a Lasentec particle size analyzer.

Using the method described above, methanol in the crystallizer and the L-threonine concentrate are mixed to produce a supersaturated state, resulting in the formation of spherical L-threonine crystals. FIG. 3 is a graph showing crystalline nucleation and agglomeration of L-threonine measured by using a Lasentec particle size analyzer, in order to analyze a crystallization mechanism in drowning-out crystallization. As shown in FIG. 3, the particle size of crystals grows during the drowning-out period, and the particle size of crystals decreases after the drowning-out period. On the other hand, the number of particles produced tends to continuously increase with time.

In the drowning-out crystallization, the storage tank in which the target material to be crystallized or the nonsolvent is put and the crystallizer in which crystallization is actually performed are maintained at a specific temperature. The temperature, volume and injection rate of reactants in the drowning-out crystallization affect the shape, size and the like of crystalline particles.

According to an embodiment of the present invention, the temperature of the concentrated filtrate containing L-threonine may be in the range of 60 to 70° C.

According to an embodiment of the present invention, the temperature of the nonsolvent may be in the range of 20 to 30° C.

According to an embodiment of the present invention, the temperature of the concentrated filtrate containing L-threonine may be 70° C., and the temperature of the nonsolvent may be 20° C.

Generally, when the temperature of the nonsolvent is increased, the size of spherical crystalline is increased. In an embodiment of the present invention, when crystallization is performed by adding the L-threonine concentrate of a temperature of 70° C. to methanol of a temperature of 20° C., large crystals can be obtained.

In addition, in the drowning-out crystallization, the amount of the nonsolvent used is important. When the amount of the nonsolvent used is reduced, a solubility reduction effect is reduced; on the other hand, when the amount of the nonsolvent used is large, the cost increases.

In an embodiment of the present invention, the volume of the nonsolvent used may be 1.0 to 3.0 times the volume of the concentrated filtrate. In an embodiment of the present invention, when the amount of methanol used is 1.0 to 3.0 times of the volume of 15-25% L-threonine concentrate, an optimized crystalline yield is obtained.

In an embodiment of the present invention, when the spherical L-threonine crystals generated by the drowning-out crystallization are separated using a separator and then dried, the spherical L-threonine crystals having a content of at least 98.5% of L-threonine can be obtained with a recovery yield of at least 95%.

In an embodiment of the present invention, the method of recovering L-threonine from the fermentation broth of a microorganism by using the nonsolvent may further include separating L-threonine crystals having an average particle size of 80 to 100 μm.

In an embodiment of the present invention, the concentrated filtrate is reacted with the nonsolvent to obtain crystalline L-threonine, and then the nonsolvent is recovered from a separated mother solution and can be reused. As illustrated in FIG. 1, the crystals are formed by the reaction of the concentrated filtrate with the nonsolvent and separated, and the nonsolvent in the mother solution remaining after separation is recovered by distillation and can be reused.

The present invention also provides crystalline L-threonine recovered from the fermentation broth of an L-threonine producing microorganism by using the nonsolvent.

The present invention also provides a feed additive containing the crystalline L-threonine recovered from the fermentation broth of an L-threonine producing microorganism by using the nonsolvent.

The crystalline L-threonine recovered from the fermentation broth by using the nonsolvent is spherical unlike the crystalline L-threonine recovered by using a conventional concentration process, thus having good flowability and high bulk density. Accordingly, when the crystalline L-threonine of the present invention is used as a feed additive, it can contribute to a reduction in transportation costs.

In an embodiment of the present invention, the recovered crystalline L-threonine may have a content of at least 98.5%, a moisture content of less than 1%, and a bulk density of 930±50 kg/m$^3$.

Hereinafter, the present invention will be described more specifically with reference to the following examples. The following examples are only for illustrative purposes and are not intended to limit the scope of the invention.

Recovery of Crystalline L-Threonine from Fermentation Broth Containing L-Threonine L-threonine producing recombinant *Escherichia coli* FTR2533 was cultured in a production medium (glucose 40 g/L, $(NH_4)_2SO_4$ 6-9 g/L, $MgSO_4$ 4-6 g/L, $KH_2PO_4$ 2-4 g/L, $FeSO_4$ 80-90 mg/L, $MnSO_4$ 10-13 mg/L, $CoCl_2$ 4-6 mg/L, $Na_2MoO_4$ 1-3 mg/L, $ZnSO_4$ 1-3 mg/L, and $H_3BO_3$ 0.3-0.8 mg/L) at 33° C. for 65 hours to produce an L-threonine containing fermentation broth. 100 L of the fermentation broth produced by fermentation was added to a membrane filter. Then, the fermentation broth was filtered by the membrane filter and a filtrate having 9.5% of L-threonine and 12.0% of total solids was obtained. The filtrate was concentrated under reduced pressure to the amount of total solids of 24.2 wt % and then stored in a raw material storage tank at a constant temperature of 70° C. Methanol in a volume 2.0 times that of the L-threonine concentrate was put in a crystallizer. Then, while the L-threonine concentrate in the raw material storage tank was added to the crystallizer at a rate of 2.0 g/min, methanol and the L-threonine concentrate were reacted in the crystallizer; the L-threonine concentrate and methanol were fully mixed using a stirrer at 300 rpm. After the total amount of the L-threonine concentrate was added to the crystallizer, the resultant mixture was stirred for 30 minutes. Then, a crystalline slurry was separated using a separator. The separated crystalline was dried in a drier at a temperature of 60° C. for 2 hours to obtain L-threonine crystals having a content of 98.5% with a recovery yield of 96%. Herein, the L-threonine product had a bulk density of 953.3 kg/m$^3$, a moisture content of 0.4%, and an inorganic material content of 0.3%.

According to the method of recovering spherical L-threonine crystals by using the nonsolvent to reduce the solubility of L-threonine in a solution, the crystals can be recovered by reducing the solubility of L-threonine in a mother solution at room temperature unlike concentration crystallization performed at a high temperature, and thus high crystalline recovery yield can be obtained. In addition, compared to conventional pillar-shaped L-threonine crystals, the spherical L-threonine crystals obtained using the nonsolvent according to the present invention have excellent flowability providing ease of packaging and handling, and a high bulk density, leading to a reduction in transportation costs, and thereby enhancing users' satisfaction.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of recovering L-threonine from a fermentation broth of an L-threonine producing microorganism, comprising:
    separating microbial bodies from the L-threonine containing fermentation broth obtained by culturing the L-threonine producing microorganisms and filtering the separated fermentation broth to obtain a filtrate;
    concentrating the filtrate; and
    reacting in a crystallizer the concentrated filtrate with a nonsolvent to obtain L-threonine spherical crystallines.

2. The method of claim 1, wherein the reacting of the concentrated filtrate with a nonsolvent is performed by adding the concentrated filtrate to the nonsolvent contained in a crystallizer or by adding the nonsolvent to the concentrated filtrate contained in a crystallizer.

3. The method of claim 1, wherein the nonsolvent is at least one solvent selected from the group consisting of methanol, ethanol, propanol, isopropanol, and mixtures thereof.

4. The method of claim 1, wherein the volume of the nonsolvent used is 1.0 to 3.0 times the volume of the concentrated filtrate.

5. The method of claim 1, wherein a temperature of the concentrated filtrate is in the range of 60 to 70° C.

6. The method of claim 1, wherein a temperature of the nonsolvent is in the range of 20 to 30° C.

* * * * *